United States Patent
Turner

(10) Patent No.: US 9,375,741 B2
(45) Date of Patent: Jun. 28, 2016

(54) STERILANT SYSTEM

(75) Inventor: Jeremy Turner, Omorokoa (NZ)

(73) Assignee: TRISTEL PLC, Snailwell, Cambridgeshire (GB)

( * ) Notice: Subject to any disclaimer, the term of this patent is extended or adjusted under 35 U.S.C. 154(b) by 9 days.

(21) Appl. No.: 14/241,971

(22) PCT Filed: Sep. 3, 2012

(86) PCT No.: PCT/GB2012/052154
§ 371 (c)(1),
(2), (4) Date: Jun. 10, 2014

(87) PCT Pub. No.: WO2013/030597
PCT Pub. Date: Mar. 7, 2013

(65) Prior Publication Data
US 2014/0326753 A1   Nov. 6, 2014

(30) Foreign Application Priority Data

Sep. 2, 2011 (GB) .................................. 1115194.1

(51) Int. Cl.
*B67D 7/70* (2010.01)
*B05B 11/00* (2006.01)
(Continued)

(52) U.S. Cl.
CPC ............... *B05B 11/3081* (2013.01); *A61L 2/18* (2013.01); *B05B 9/0426* (2013.01);
(Continued)

(58) Field of Classification Search
CPC . B05B 11/3081; B05B 11/0054; B65D 81/32
USPC .............. 222/138, 214, 383.2, 183, 131, 136, 222/105, 94
See application file for complete search history.

(56) References Cited

U.S. PATENT DOCUMENTS

| 3,554,674 A | 1/1971 | Huret |
| 4,067,479 A | 1/1978 | Moline |

(Continued)

FOREIGN PATENT DOCUMENTS

| CN | 101524631 | 9/2009 |
| CN | 201537558 | 8/2010 |

(Continued)

OTHER PUBLICATIONS

International Preliminary Report on Patentability from International Application No. PCT/GB2012/052154 mailed Mar. 5, 2014.

(Continued)

*Primary Examiner* — Donnell Long
(74) *Attorney, Agent, or Firm* — Merchant & Gould P.C.

(57) ABSTRACT

A multi-part sterilant system (12) comprising:
 a first part (4) comprising a first reagent in a carrier medium in a first container (6);
 a second part (8) comprising a second reagent in a carrier medium in a second container (10);
 wherein the first reagent and the second reagent will react to provide a sterilizing composition when the first part (4) is mixed with the second part (8);
 a pump head (2) having a peristaltic pump member (22);
 the first container (6) having a first-part dispensing tube (16) extending from its interior and disposed through the pump head (2);
 the second container (10) having a second-part dispensing tube (18) extending from its interior and disposed through the pump head (2);
 wherein the peristaltic pump member (22) when actuated acts on both the first-part dispensing tube (16) and the second-part dispensing tube (18) so as simultaneously to pump substantially equal volumes of the first part (4) and the second part (8).

17 Claims, 12 Drawing Sheets

(51) Int. Cl.
*A61L 2/18* (2006.01)
*B05B 9/08* (2006.01)
*B65D 81/32* (2006.01)
*B05B 9/04* (2006.01)

(52) U.S. Cl.
CPC .......... *B05B 9/0872* (2013.01); *B05B 11/0008* (2013.01); *B05B 11/0054* (2013.01); *B05B 11/303* (2013.01); *B05B 11/3084* (2013.01); *B65D 81/32* (2013.01); *A61L 2202/15* (2013.01); *A61L 2202/16* (2013.01); *B05B 9/042* (2013.01)

(56) References Cited

U.S. PATENT DOCUMENTS

| | | | |
|---|---|---|---|
| 4,214,681 A | | 7/1980 | Levine |
| 4,232,828 A | | 11/1980 | Shelly, Jr. |
| 4,271,988 A | | 6/1981 | Clausen |
| 4,921,150 A | * | 5/1990 | Lagergren et al. ............ 222/639 |
| 5,152,431 A | * | 10/1992 | Gardner et al. ............... 222/136 |
| 5,398,846 A | * | 3/1995 | Corba et al. .................... 222/1 |
| 5,402,916 A | * | 4/1995 | Nottingham et al. ......... 222/134 |
| 5,498,191 A | | 3/1996 | DeMars |
| 6,193,058 B1 | | 2/2001 | Yacko et al. |
| 6,364,105 B1 | | 4/2002 | Yacko et al. |
| 6,510,965 B1 | * | 1/2003 | Decottignies et al. .......... 222/95 |
| 7,281,643 B2 | * | 10/2007 | Lin ............................... 222/214 |
| 2004/0089745 A1 | | 5/2004 | Zimmerman |
| 2004/0213684 A1 | | 10/2004 | Klein |
| 2005/0048598 A1 | | 3/2005 | Guenec et al. |
| 2005/0150905 A1 | * | 7/2005 | van der Heijden ............ 222/135 |
| 2007/0068966 A1 | * | 3/2007 | Orzech et al. ................. 222/136 |
| 2010/0122992 A1 | | 5/2010 | Vellutato, Sr. et al. |
| 2010/0313996 A1 | | 12/2010 | Breault et al. |
| 2011/0190635 A1 | | 8/2011 | Bosler |

FOREIGN PATENT DOCUMENTS

| | | | |
|---|---|---|---|
| CN | 201537558 U | * | 8/2010 |
| DE | 100 50 182 | | 11/2001 |
| EP | 0 118 601 | | 9/1984 |
| EP | 1 184 071 | | 3/2002 |
| EP | 1 186 574 | | 3/2002 |
| EP | 1 661 587 | | 5/2006 |
| EP | 1 889 665 | | 2/2008 |
| FR | 2 520 639 | | 8/1983 |
| GB | 1 430 403 | | 3/1976 |
| JP | 2002119839 | | 4/2002 |
| WO | WO 90/08558 | | 8/1990 |
| WO | WO 2005/112634 | | 12/2005 |
| WO | WO 2006/079822 | | 8/2006 |

OTHER PUBLICATIONS

International Search Report and Written Opinion from International Application No. PCT/GB2012/052154 mailed Aug. 6, 2013.

* cited by examiner

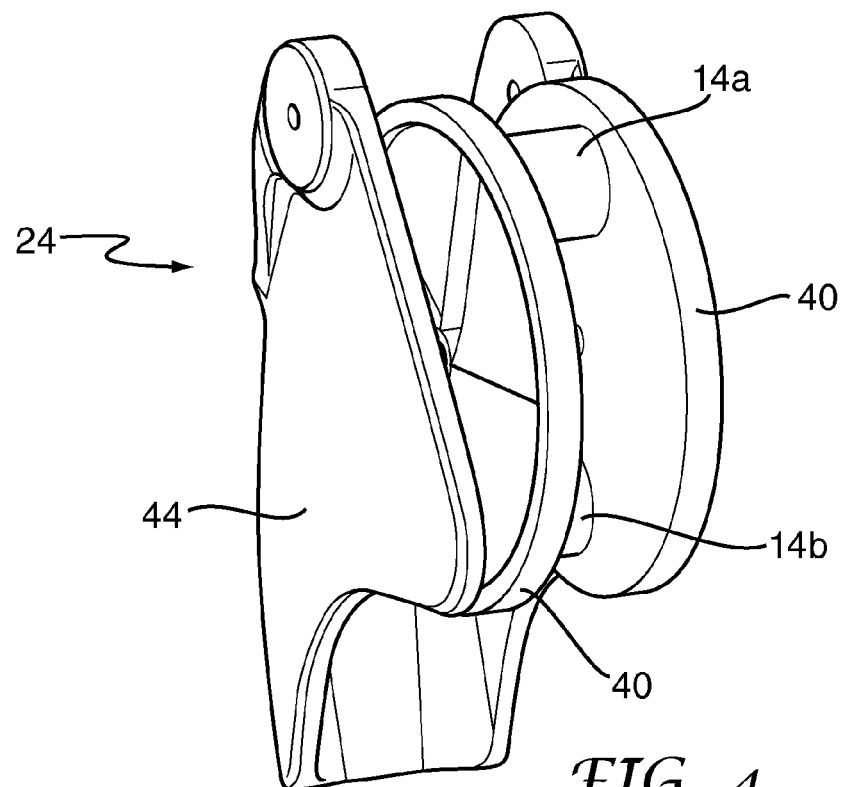
FIG. 4
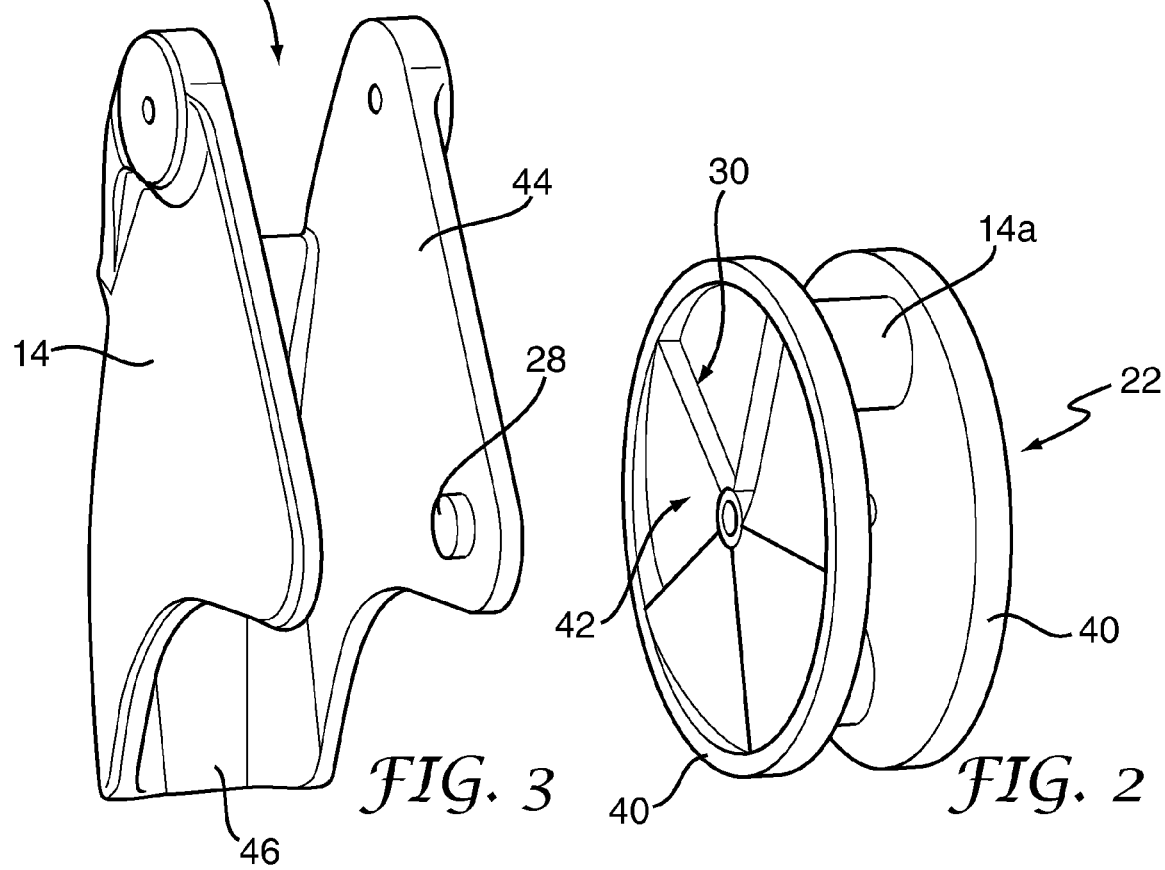
FIG. 3
FIG. 2

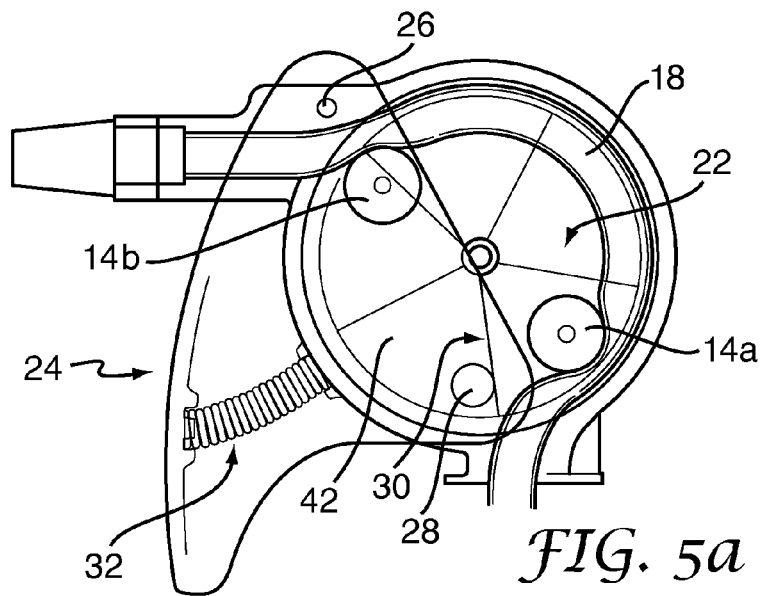
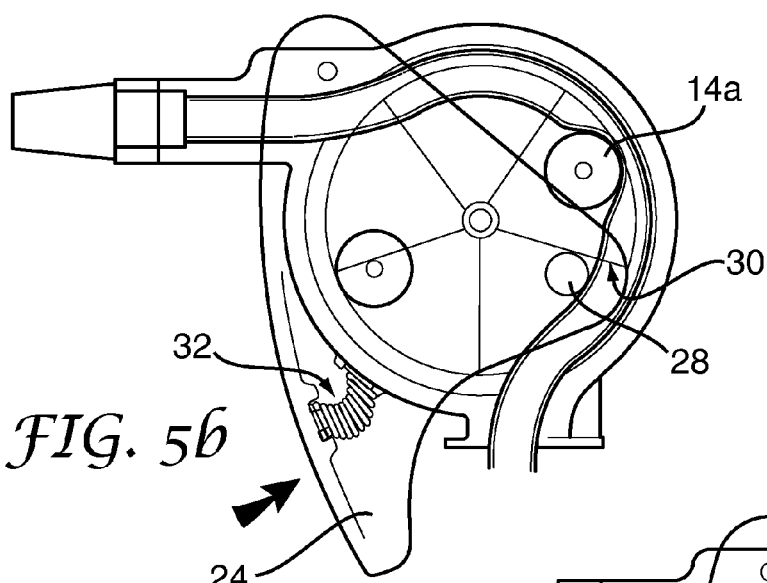
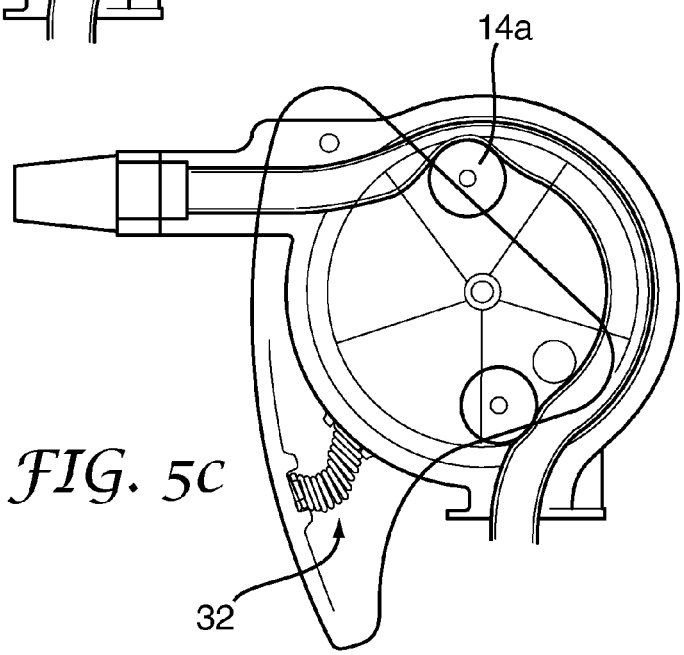

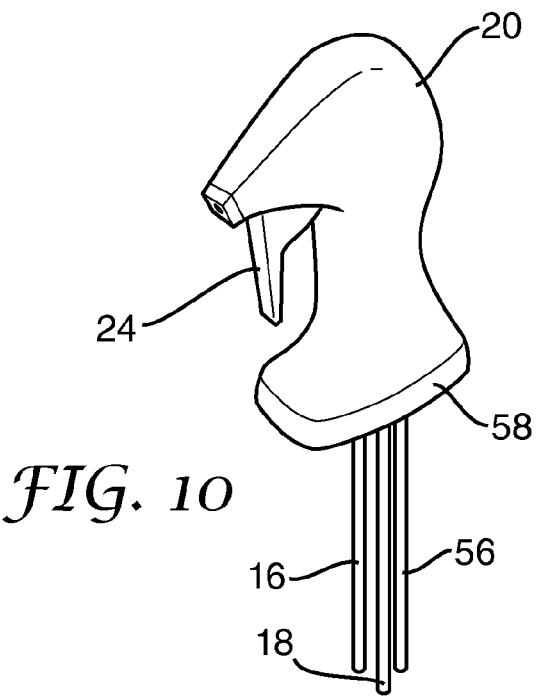
FIG. 10
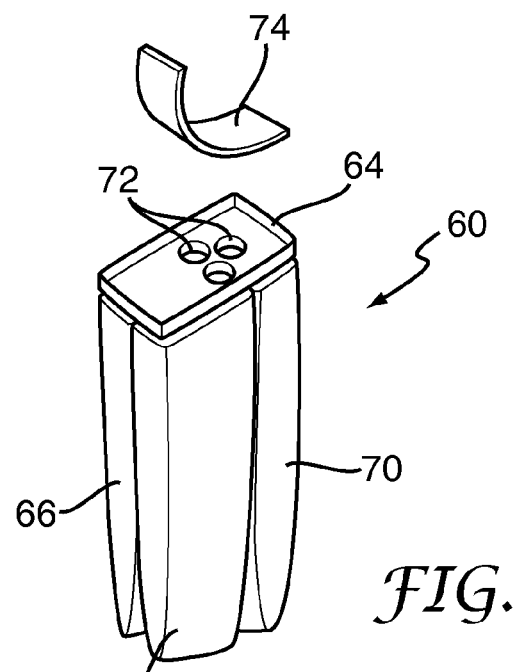
FIG. 12
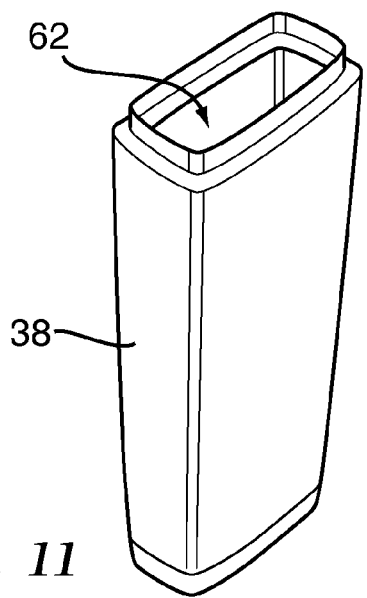
FIG. 11
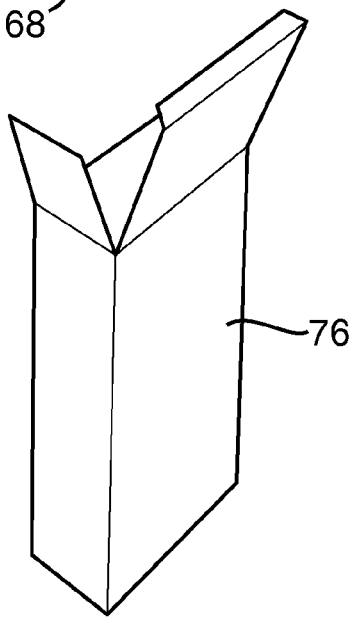

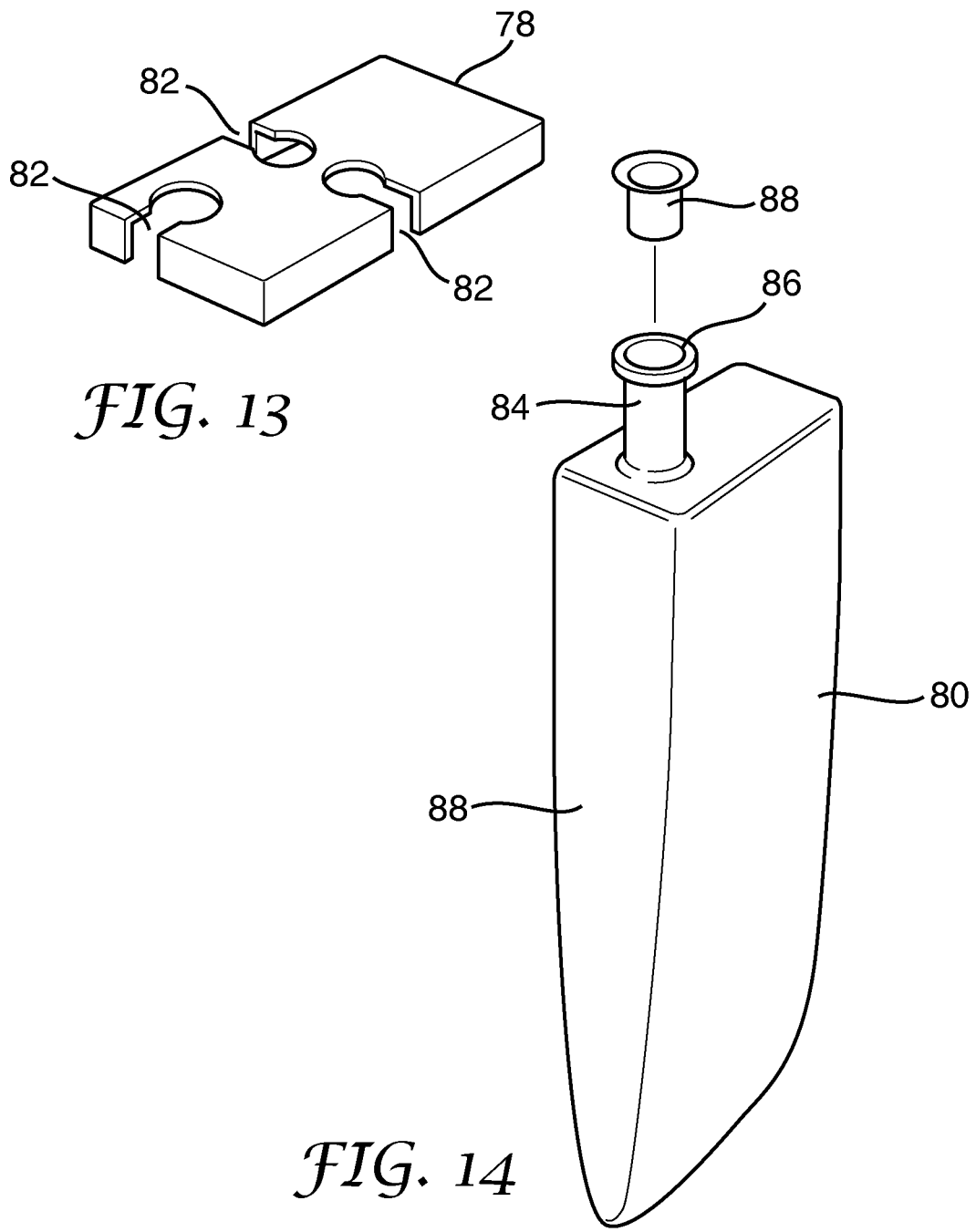

STERILANT SYSTEM

This application is a National Stage Application of PCT/GB2012/052154, filed 3 Sep. 2012, which claims benefit of Serial No. 1115194.1, filed 2 Sep. 2011 in the United Kingdom and which applications are incorporated herein by reference. To the extent appropriate, a claim of priority is made to each of the above disclosed applications.

BACKGROUND a. Field of the Invention

The present invention relates to a sterilant system and method for sterilising surfaces.

b. Related Art

Two-part sterilising solutions are used in applications where the active sterilising ingredient is unstable over time. The solution is therefore prepared in situ shortly before it is to be used. A particularly important sterilising agent is chlorine dioxide ($ClO_2$), which may be formed from mixtures of various reagents including: chlorite and acid; chlorate, peroxide and acid; and chlorite, hypochlorite, and a suitable buffer. Chlorine dioxide has excellent sterilising and bactericidal properties, and oral ingestion in man and animals has been shown to be relatively safe.

WO 2006/079822 describes a two part sterilant system having two reagents, each of which is put up in an aqueous medium in its own container. The aqueous media contain a foam promoter, and actuation of a single trigger dispenses each part as a foam. Mixing of the foams allows the reagents to react together to form a sterilant such as $ClO_2$ in situ.

The effectiveness of two-part sterilant systems in conventional trigger sprayers can be reduced if the spray action does not result in the delivery of an identical volume of each reagent medium, resulting in an excess of one reagent in the mixture. Delivery of different volumes is particularly likely to result when the dispensed media are of different viscosities.

SUMMARY OF THE INVENTION

Aspects of the invention are specified in the independent claims. Preferred features are specified in the dependent claims.

The invention allows plural volumes of fluid to be evenly pumped as equal volumes from two or more sources irrespective of differences in viscosity.

Another advantage of the invention over conventional multi-component fluid pumps is that it ensures clean delivery of each fluid. Prior art sterilant apparatuses typically have pistons and require use of silicone oil or a similar lubricant. Such lubricants can contaminate the fluids being pumped. In the present invention, silicone and other lubricants are not required, and the fluids being pumped are isolated from contact with the pump member.

BRIEF DESCRIPTION OF THE DRAWINGS

The invention will now be further described, by way of example only, with reference to the following drawings, in which:

FIGS. 2 and 3 show, respectively, the trigger and the peristaltic pump member of the assembly of FIG. 4;

FIG. 4 is a view of the assembled trigger and peristaltic pump member of the apparatus of FIG. 1;

FIGS. 5a-5c show partial side views of the apparatus of FIG. 1;

FIGS. 10 and 11 show, respectively, a pump head and a container housing of a multi-part sterilant system in accordance with a further embodiment of the invention;

FIG. 12 shows a refill comprising collapsible containers suitable for insertion into the container housing of FIG. 11;

FIG. 13 shows a collar portion of a refill, for securing collapsible containers together, according to a further embodiment of the invention;

FIG. 14 shows a collapsible container suitable for engaging with the collar portion of FIG. 13.

DETAILED DESCRIPTION

Figure 1:
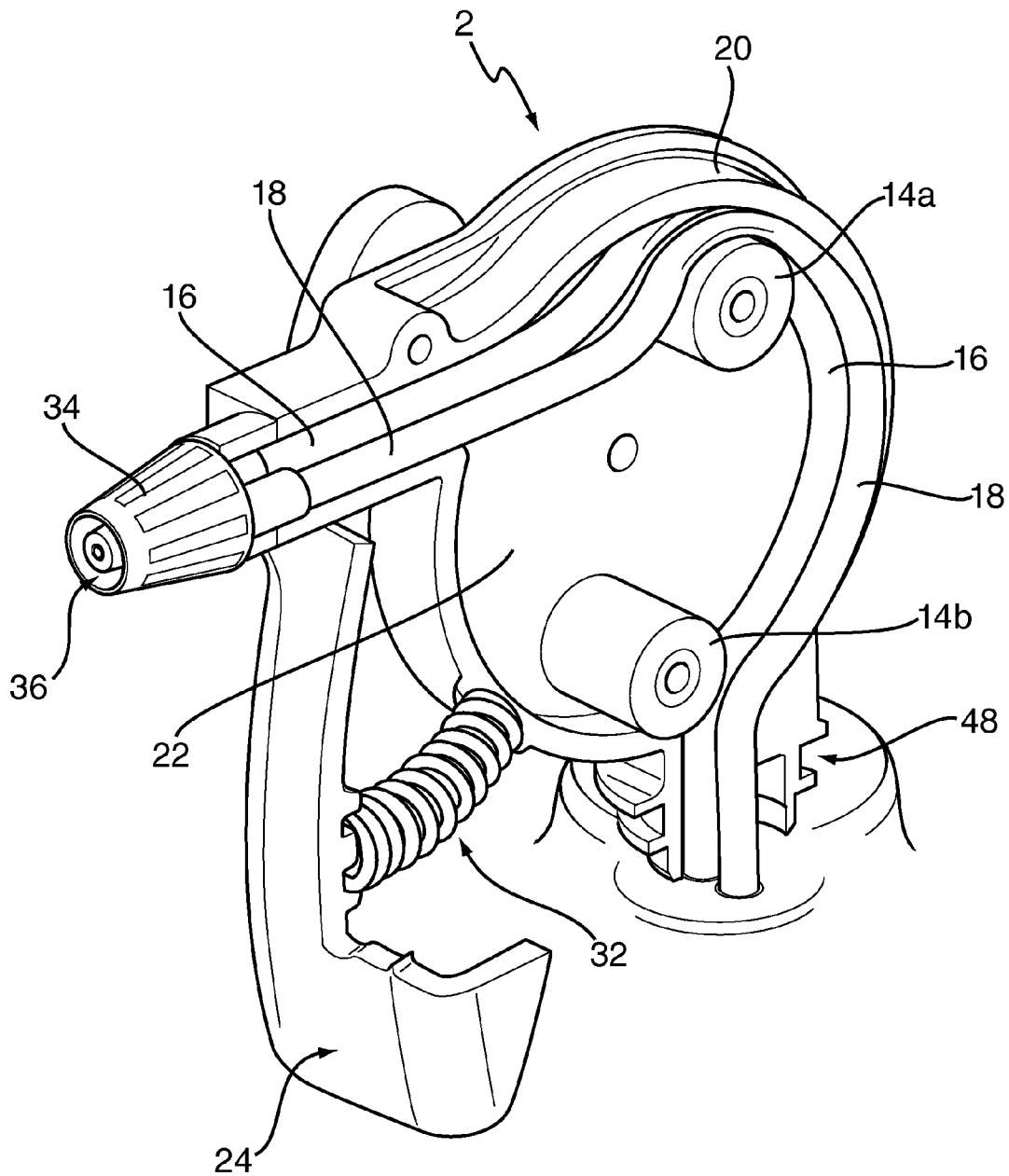
FIG. 1 is a cutaway view of a pump apparatus of the sterilant system of FIG. 6.

Referring to FIG. 1, a pump apparatus 2 includes a pump head 20, a peristaltic pump member 22, and a plurality of dispensing tubes 16,18 disposed through the pump head 20. In this embodiment, the peristaltic pump member 22 is a rotor which is rotatably housed within the pump head 20; however, it will be understood that other types of peristaltic pump member 22 could be used, for example a translational pump member. In this example, two dispensing tubes 16,18 are provided side by side, for simultaneously dispensing two liquids or gels. Three or more dispensing tubes could be used in alternative embodiments, for simultaneously dispensing a corresponding number of fluids.

When actuated, the peristaltic pump member 22 acts simultaneously on each of the dispensing tubes 16,18, in this embodiment via one or more impellers 14. Two impellers 14a,14b are illustrated. Rotation of the pump member 22 causes at least one of the impellers 14 to act on each of the dispensing tubes 16,18 so as simultaneously to pump a fluid through each dispensing tube.

Each dispensing tube 16,18 is squeezed by the impeller 14 against an inner surface of the pump head 20, and as the pump member 22 turns, the impeller 14 drives fluid ahead of it through the dispensing tubes. Because the volume squeezed out by the impeller 14 is independent of the viscosity of the fluid within a dispensing tube, a substantially equal volume of fluid is pumped through each dispensing tube 16,18 regardless of viscosity. The dispensing tubes 16,18 are elastomeric at least in the region where the impeller 14 acts upon them, to ensure that the tubes return to their original cross-sectional shape when not acted upon by an impeller. In a preferred embodiment, each dispensing tube 16, 18 is elastomeric along its entire length. In this embodiment, each dispensing tube 16, 18 is of a unitary construction.

In the present example, the pump head 20 is provided with a nozzle housing 34. The dispensing tubes 16,18 terminate at a nozzle 36, secured in the nozzle housing 34 through which fluids from both tubes are dispensed. The fluids may mix substantially at the point of exit from the nozzle 36 or some distance before. In other embodiments, each dispensing tube terminates in a separate nozzle outlet so that mixing of fluids does not occur until after the fluids have been dispensed by the pump apparatus.

The exemplified pump apparatus 2 includes a finger-operated trigger 24 which is pivotally mounted to the pump head 20 and provided with a return spring 32 which urges the trigger 24 to an extended position. A user pulls the trigger 24 to actuate the peristaltic pump member 22 as will be described below.

Referring now to FIG. 2, the exemplified peristaltic pump member 22 comprises two opposed drive wheels 40 which are connected together by the impellers 14. The outer face of each drive wheel 40 is provided with ratchet surfaces 30 which are upstanding from adjacent transitional flat surfaces 42. Each transitional flat surface 42 slopes evenly between an outer edge of one ratchet surface and an inner edge of an adjacent ratchet surface. In this embodiment the trigger 24 (FIG. 3) is generally symmetric about a vertical axis, having a front portion 46 and a pair of opposed side arms 44. Each side arm 44 is provided with an inwardly-directed pawl 28 for engagement with a ratchet surface 30 of the pump member 22 when the pump member 22 is housed within the pump head 20 between the arms 44 of the trigger 24 (FIG. 4).

FIGS. 5a-5c show stages of operation of the pump apparatus. Starting from a fully extended position, a user squeezes the trigger 24 which pivots about a pin 26. Each pawl 28 moves over a sloping transitional surface 42 until it abuts a ratchet surface 30 (FIG. 5a). Further squeezing of the trigger causes each pawl 28 to push against a ratchet surface 30 and drive the pump member anticlockwise as viewed. This turning first brings one of the impellers 14a simultaneously into contact with both dispensing tubes 16,18, and then causes the impeller 14a to begin pumping substantially equal volumes of fluid from each dispensing tube (FIG. 5b). After the trigger has been fully pulled and released by the user, the return spring 32 brings the trigger back to its fully extended position, causing each pawl 28 to disengage from a ratchet surface 30 and pass back over the sloping transitional surface 42 (FIG. 5c) until it drops over an adjacent ratchet surface 30. During the trigger's return, the pump member 22 does not move and pumping stops. A further operation of the trigger repeats the pumping process. In this embodiment, each drive wheel 40 has five ratchet surfaces 30. In other embodiments, the number of ratchet surfaces may be selected to permit reliable pumping of smaller volumes of fluids; for example by allowing a user optionally to pull the trigger only half way towards the pump housing before releasing it. In other embodiments the number of ratchet surfaces 30 may be selected to provide desired increments/doses or multiples of up to 20-30.

Figure 6:
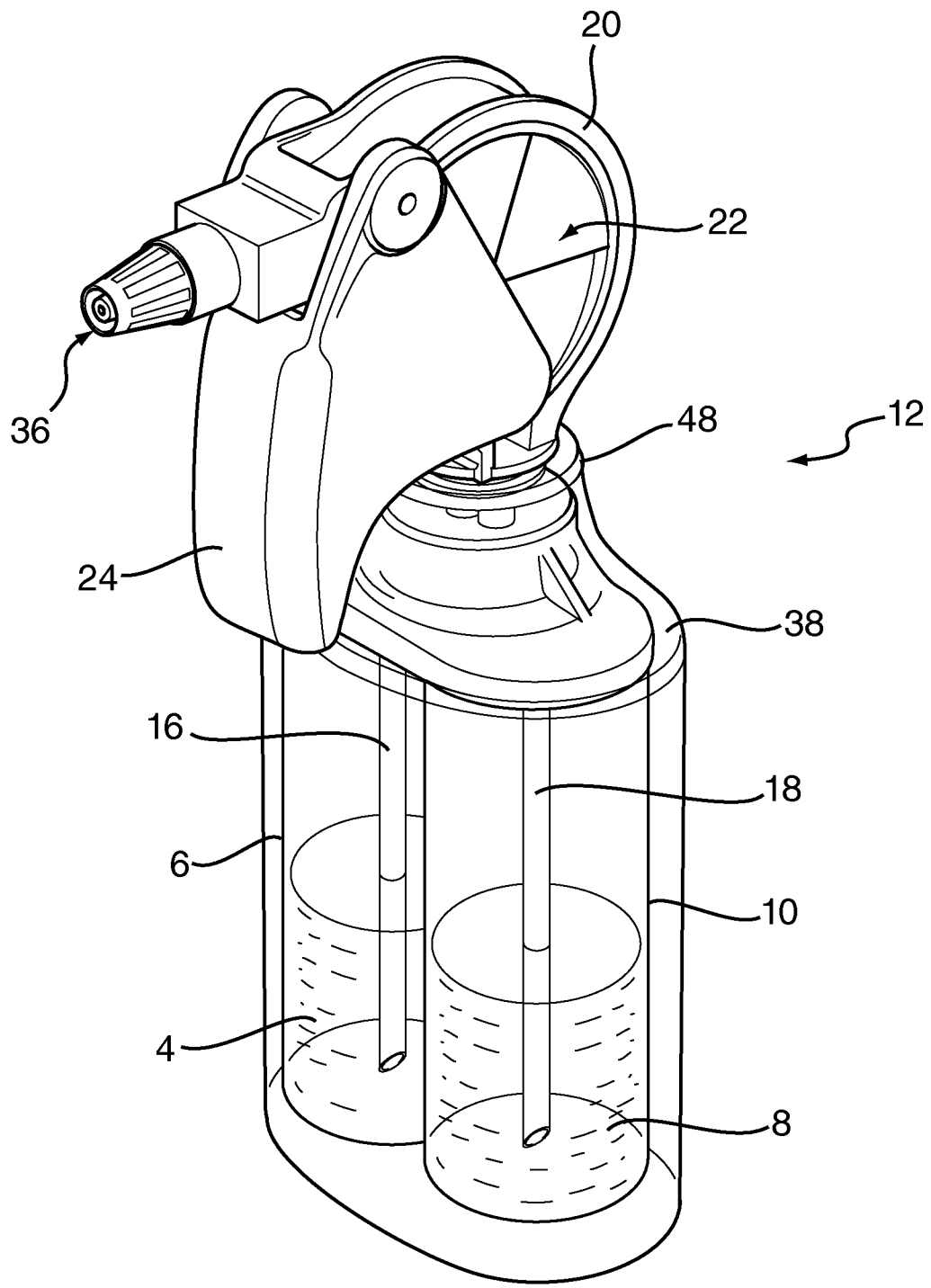
FIGS. 6 and 7 illustrate a multi-part sterilant system in accordance with an aspect of the invention.
Figure 7:
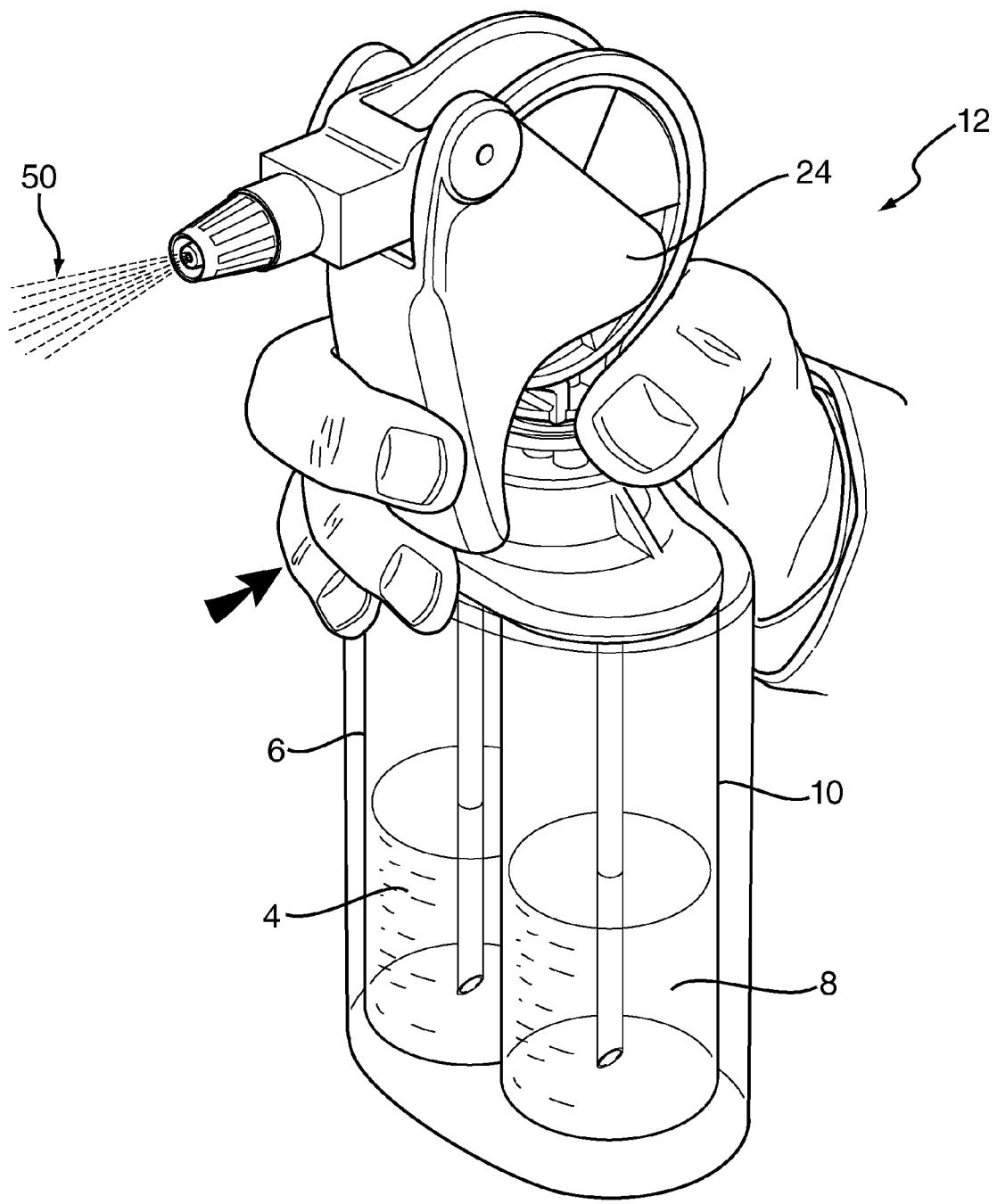

Referring now to FIGS. 6 and 7, a preferred embodiment of the invention provides a two-part sterilant system 12 which incorporates the previously-described peristaltic pump apparatus. The sterilant system 12 comprises a first part 4 and a second part 8. The first part 4 is in a first container 6 and comprises a first reagent in a carrier medium. The second part 8 is in a second container 10 and comprises a second reagent in a carrier medium. The first reagent and the second reagent react when the first and second parts are mixed, to provide a sterilising composition. Those skilled in the art of sterilant formulations will understand that the first and second reagents may be selected from a variety of substances. In a preferred embodiment the reagents react to produce $ClO_2$. The first part may, for example, comprise an aqueous solution of a chlorite such as sodium chlorite, and the second part may comprise an aqueous acid or mixture of acids.

The sterilant system 12 has a pump head 20 with a peristaltic pump member 22. The first 6 and second 10 containers in this embodiment are housed in a container housing 38 which is secured to the pump head 20 by means of a securing feature 48 on the pump head which engages with an internal surface of the container housing 38. In one embodiment, the securing feature is a locking push-fit, and once the container housing is engaged, it is not removable; the sterilant system 12 is disposable and will be discarded once the contents have been discharged. In alternative embodiments, the container housing 38 and the containers 6, 10 can be exchanged to permit refilling of the contents.

The first container 6 has a first-part dispensing tube 16 extending from its interior and disposed through the pump head 20. The second container 10 has a second-part dispensing tube 18 extending from its interior and disposed through the pump head 20. When the peristaltic pump member 22 is actuated by a user operating the trigger 24, the pump member 22 acts simultaneously on both the first-part dispensing tube 16 and the second-part dispensing tube 18, as described with reference to FIGS. 1-5, so as simultaneously to pump substantially equal volumes of the first part 4 and the second part 8 as a spray 50 of liquid, gel or foam.

Figure 8:
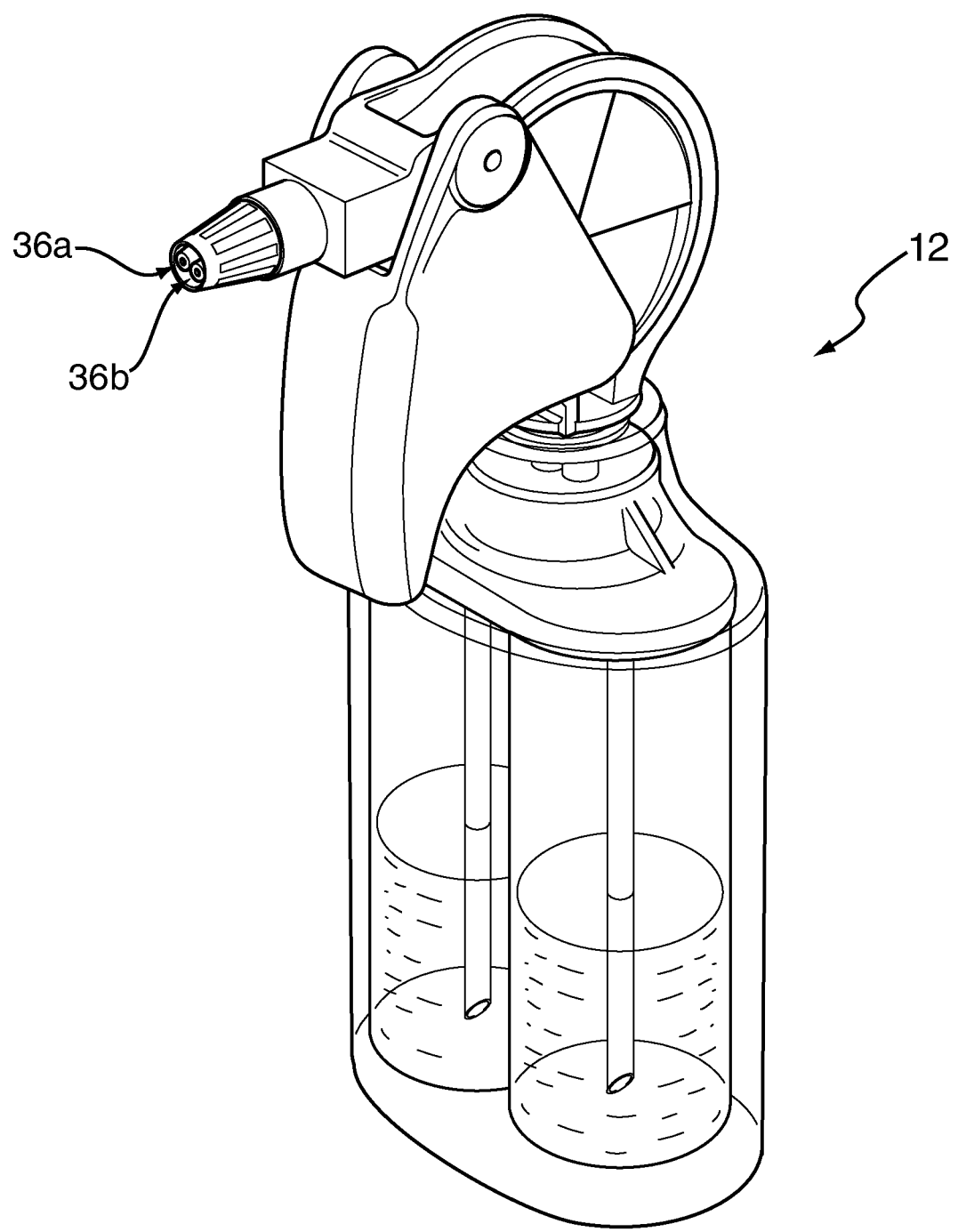
FIG. 8 shows a multi-part sterilant system in accordance with another embodiment of the invention.

In this embodiment, the first-part dispensing tube 16 and the second-part dispensing tube 18 are connected together at their free ends to a nozzle 36 through which is pumped a mixture of the first part 4 and the second part 8 when the pump member 22 is actuated. In the embodiment of FIG. 8, each dispensing tube 16,18 has its own nozzle 36a,36b so that the first part and the second part are pumped as separate sprays or jets of fluid which will be mixed in situ, for example by a user rubbing his hands together when the system is a hand sanitizer or hand cleaner, or with a cloth or wipe when the system is used to sterilize a surface, for example a surface in a hospital or other clinical environment.

It will be appreciated that, within practical limits, any number of dispensing tubes may be employed for simultaneously dispensing a plurality of fluids. The invention allows a variety of different reagents and/or ingredients or additives to be combined at or shortly before the point of delivery. Thus, components which individually have desirable properties but which may be unstable when stored in solution together may be employed in the multi-part system. A practical limit of up to about 10 dispensing tubes and associated containers is envisaged; for example 4-6 tubes, or for particularly complex systems, 7-9 tubes.

Figure 9:
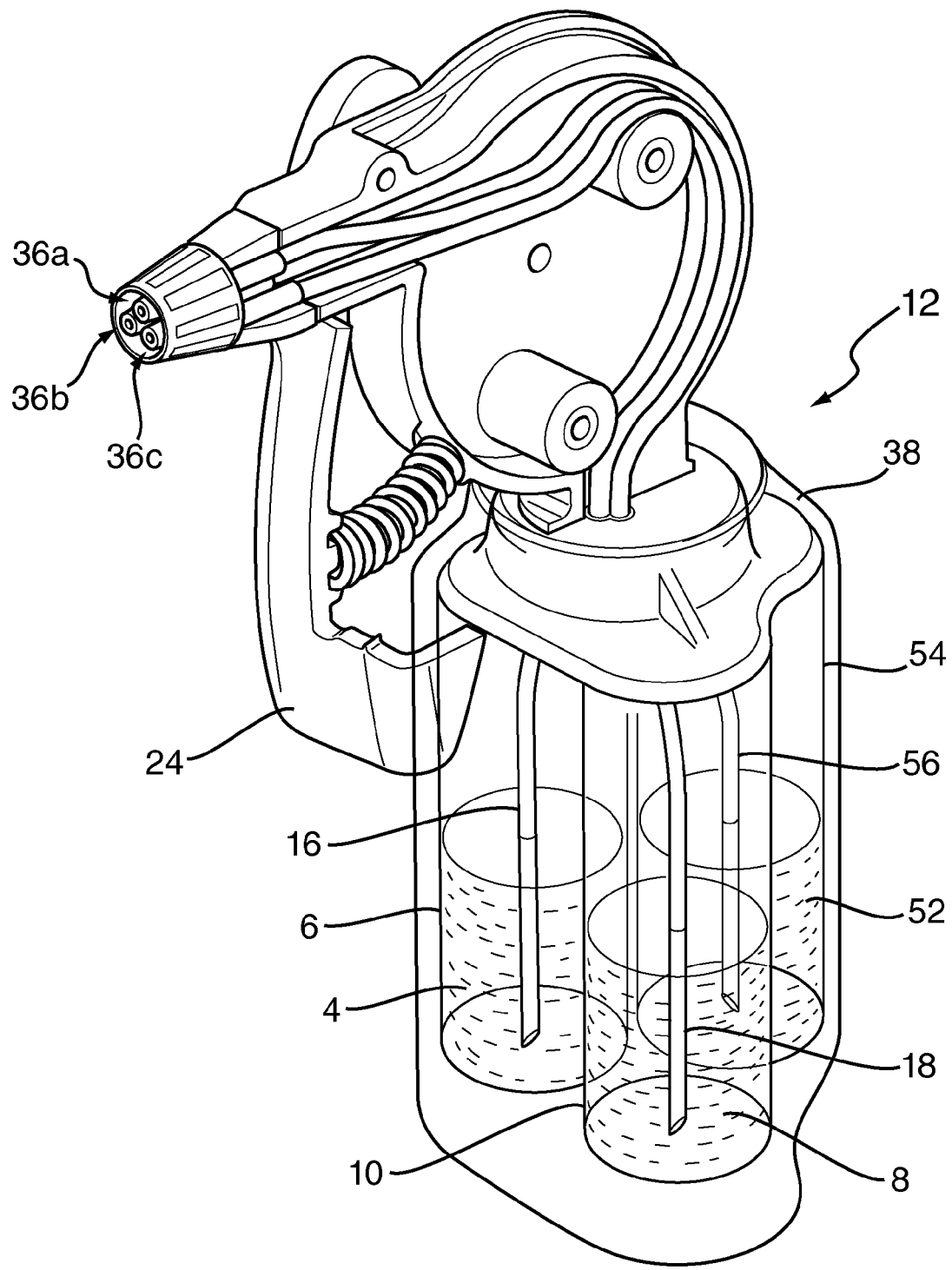
FIG. 9 shows a multi-part sterilant system in accordance with a further embodiment of the invention.

Referring now to FIG. 9, an embodiment of a multi-part sterilant system 12 is illustrated. This system is similar to the system of FIGS. 6-8, but includes a third part 52 in a third container 54, with a third dispensing tube 58. Equal volumes of each part 4,8,52 are simultaneously dispensed when the trigger 24 is squeezed, via respective nozzles 36a,b,c. The first part and the second part may include reagents which react when mixed to provide an oxidising sterilant composition, for example $ClO_2$, and the third part may include additional components which may not be stable to long term exposure to either or both of the reagents. In this example, the third part comprises an alcohol, notably isopropanol, which provides additional antiseptic functionality. Other alcohols, or mixtures of alcohols, may be used.

To increase the proportion of alcohol, or other desired component, in the dispensed mixture, it will be appreciated that additional dispensing tubes may be used. For example, a fourth dispensing tube may be used, and both the third and fourth dispensing tubes may be used to dispense alcohol, providing up to 50% alcohol in the final mixture without alcohol being present in the first part or the second part. A fifth dispensing tube permits up to 60% alcohol to be dispensed, and use of 10 tubes permits up to 80% alcohol to be dispensed. When a plurality of dispensing tubes are used to dispense the same component, for example alcohol, this component may optionally be provided in fewer containers than the number of dispensing tubes for the component. For example, a single container may be used, in which two or more dispensing tubes are disposed. For efficiency, the volume of such a container is preferably increased in proportion to the number of associated dispensing tubes so that each container is emptied after the same number of operations of the trigger.

Each container 6,10,54 may be provided with a vent tube to connect the top of the container's interior to atmosphere to allow pressure equalisation within the container during the pumping process. The vent tubes may be provided with a non-return valve to ensure that air can enter but fluid cannot exit through the vent tubes. Alternatively, each container may be collapsible so that as fluid is pumped out, the internal volume of the container contracts. The containers may be collapsible by being formed from a flexible material such as a thin plastics material, or by virtue of being provided with flexible joints or folds, for example bellows-fashion.

Figure 15:
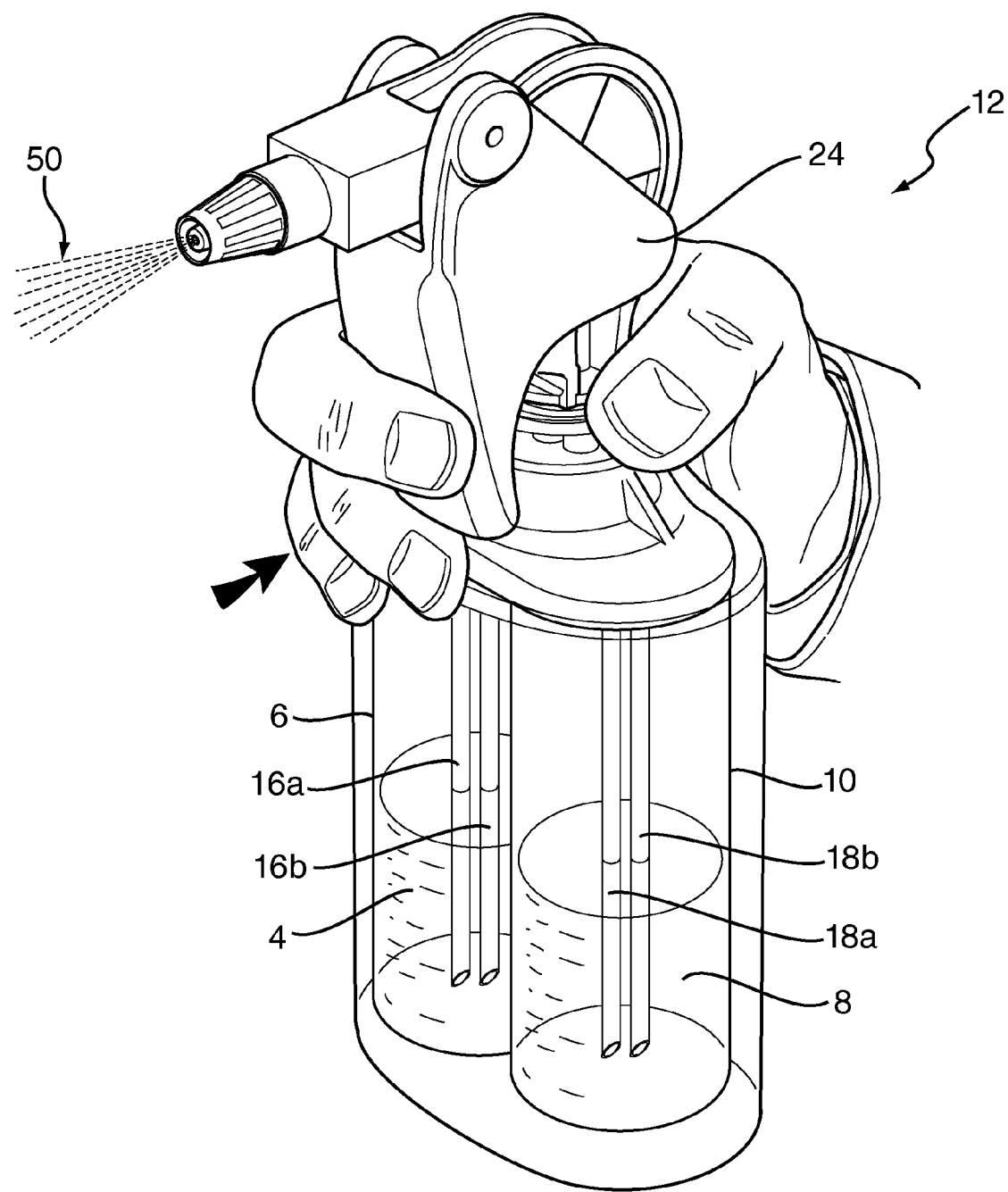
FIGS. 15-17 illustrate other embodiments of the invention.

We have found that the size of the pump head needed may be reduced by using a plurality of first-part dispensing tubes 16 and second-part dispensing tubes 18. By using a plurality of dispensing tubes (for example, two or three) for each part, each tube may be of narrower internal and external dimensions for delivery of the same volume as is achievable using a single tube of larger dimensions for each part. The narrower tubes can conform to a smaller radius than wider tubes, which allows the radius of the peristaltic pump member 22 and pump head 20 to be correspondingly reduced, making it easier to hold and operate. Each type of the plurality of dispensing tube may be housed in a single container; alternatively a plurality of first containers 6 and/or second containers 10 may be provided. An embodiment which uses two first-part dispensing tubes 16a,16b and two second-part dispensing tubes 18a,18b is illustrated in FIG. 15.

FIGS. 10 to 12 show an example of a multi-part sterilant system including collapsible containers. The pump head 20 is as described previously and includes three dispensing tubes 16, 18, 56 extending from a base portion 58 of the pump head 20.

The container housing 38 is sized to receive a refill component 60 as described below and includes an opening 62 at a top of the housing 38. The container housing 38 is preferably made from a substantially rigid material, although the container housing 38 may be at least partially deformable, at least to permit engagement of the housing 38 with the pump head 20.

FIG. 12 shows an embodiment of a refill component 60 including a chassis or collar portion 64 and three collapsible containers 66, 68, 70. The collapsible containers 66, 68, 70 perform substantially the same function as the containers 6, 10, 54 previously described and, in particular, each container 66, 68, 70 includes a reagent or part of the multi-part sterilant system. Each of the containers 66, 68, 70 is preferably made from a thin wall of a plastics material such as polyvinyl chloride (PVC).

An opening (not shown) in an upper region of each of the containers 66, 68, 70 is in fluid communication with an aperture 72 in the collar portion 64. Preferably, the collar portion 64 includes the same number of apertures 72 as the number of containers 66, 68, 70. The apertures 72 are located such that when the openings in the containers 66, 68, 70 are aligned with the apertures 72, the containers 66, 68, 70 are held in a suitable arrangement beneath the collar 64. In this way, the collar portion 64 secures the containers in such a way that the dispensing tubes 16, 18, 56 may be inserted into the containers 66, 68, 70 through the apertures 72 in the collar 64, preventing cross-contamination of the dispensing tubes 16, 18, 56 when replacing the refill 60.

The sterilant system is assembled by lowering the containers 66, 68, 70 into the container housing 38 and inserting the dispensing tubes 16, 18, 56 into the containers 66, 68, 70 through the apertures 72 in the collar 64. The collar portion 64 engages with one or both of the base portion 58 of the pump head 20 and the opening 62 of the container housing 38, such that the containers 66, 68, 70 are substantially suspended within the housing 38.

As liquid is drawn from the containers 66, 68, 70, through actuation of the trigger 24 and pump member 22, the containers 66, 68, 70 collapse. This provides a system that minimises or prevents the evaporation of liquid and the release of odours from the containers 66, 68, 70, which is particular desirable in the case of more volatile reagents that may be used in the sterilant system.

It is envisaged that the pump head 20 and container housing 38 will be reused, and the refill component 60 replaced as described above. It is, therefore, preferable to supply the refill 60 with a seal 74 covering the apertures 72 in the collar 64. The seal 74 would then be removed during assembly of the sterilant system. Preferably the refill component 60 is supplied in a relatively rigid box or container 76, such as a cardboard box, to prevent deformation of the collapsible containers 66, 68, 70.

FIGS. 13 and 14 show a collar portion 78 and collapsible container 80 according to a further embodiment of the invention.

The collar portion 78 (FIG. 13) is sized to engage with one or both of the base portion 58 of the pump head 20 and the opening 62 of the container housing 38, and the collar 78 includes three slots 82, each slot 82 extending inwards from an edge of the collar 78. The slots 82 are sized to receive a neck portion 84 of a collapsible container 80. The collapsible container 80 (FIG. 14) is substantially the same as the collapsible containers 66, 68, 70 previously described. The container 80 includes a neck portion 84 extending from an upper region of the container 80, the neck portion 84 having a lip 86 around a top edge furthest from a body 88 of the container.

The neck portion 84 and lip 86 of the container 80 are sized to be received within a slot 82 in the collar 78. When the neck portion 84 is fully engaged in the collar 78, the lip 86 rests against a surface of the collar 78, allowing the container 80 to be suspended from the collar 78.

To seal the container 80 during transport and storage, a bung 88 may be inserted into the top of the neck portion 84. This bung 88 can then be removed during assembly of the sterilant system to allow a dispensing tube 16 to be inserted into the container 80.

Figure 16:
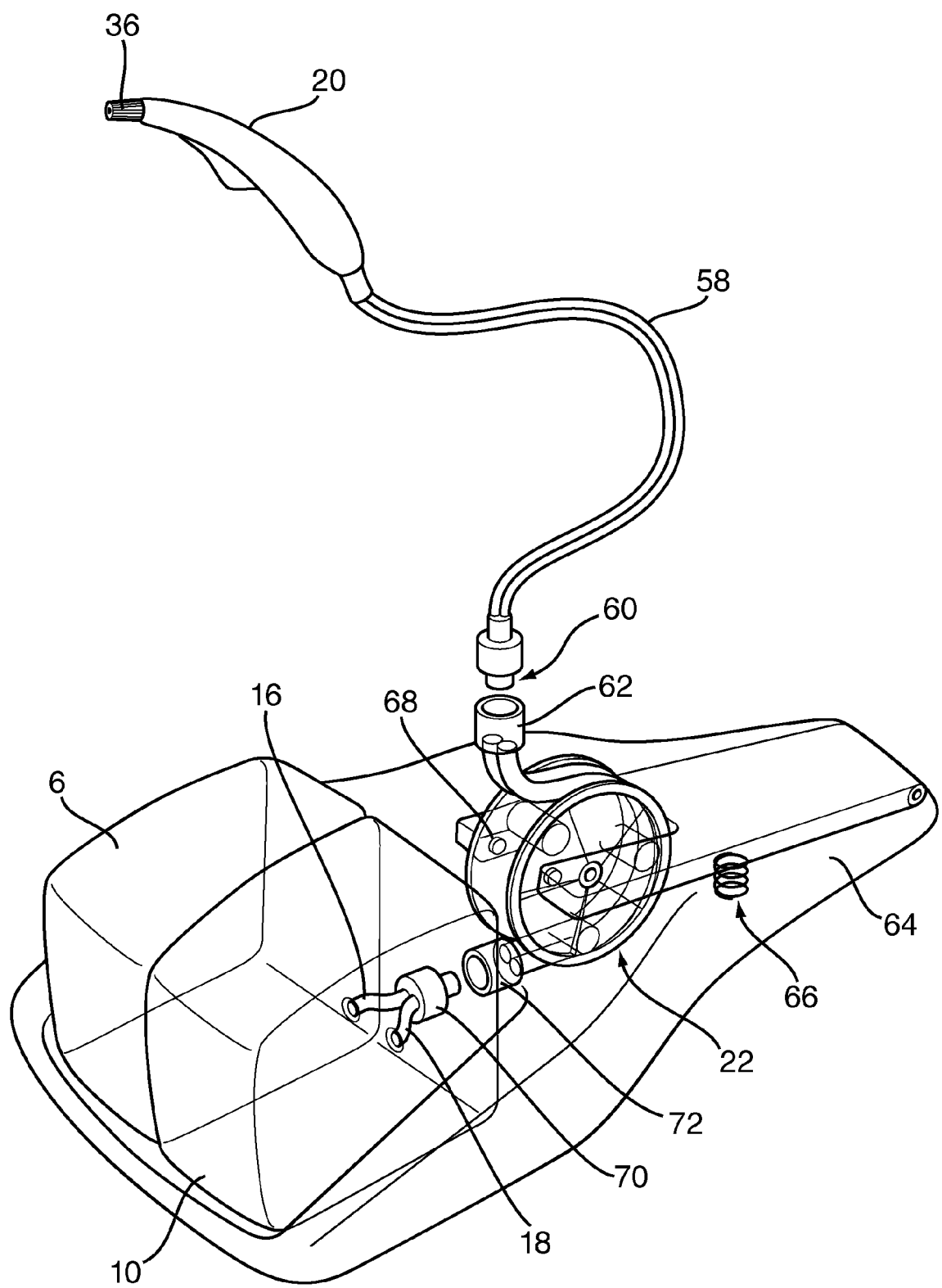

Referring now to FIG. 16, a foot-operated embodiment of the invention is illustrated. This permits the weight of the pump mechanism, including reagents and containers 6,10 to be supported on the ground, allowing a user to carry only the pump head 20. In this embodiment, the peristaltic pump member 22 is operated by the action of a user's foot on a footpad 64 which is return-biased by a spring 66. A spring-loaded catch 68 on the end of the foot pad pushes the pump ratchet to turn the pump member. The containers 6,8 are removable and replaceable, and are connected to tubes in the peristaltic pump member 22 by a connector 70 on the containers and a corresponding connector 72 on the pump member. The pump head 20 receives pumped fluids via a supply hose 58. In this embodiment, the supply hose 58 is detachable from the footpad and connectable via a hose plug 60 and hose socket 62. The hose 58 may be detached for replacement or cleaning of the pump head 20.

Figure 17:
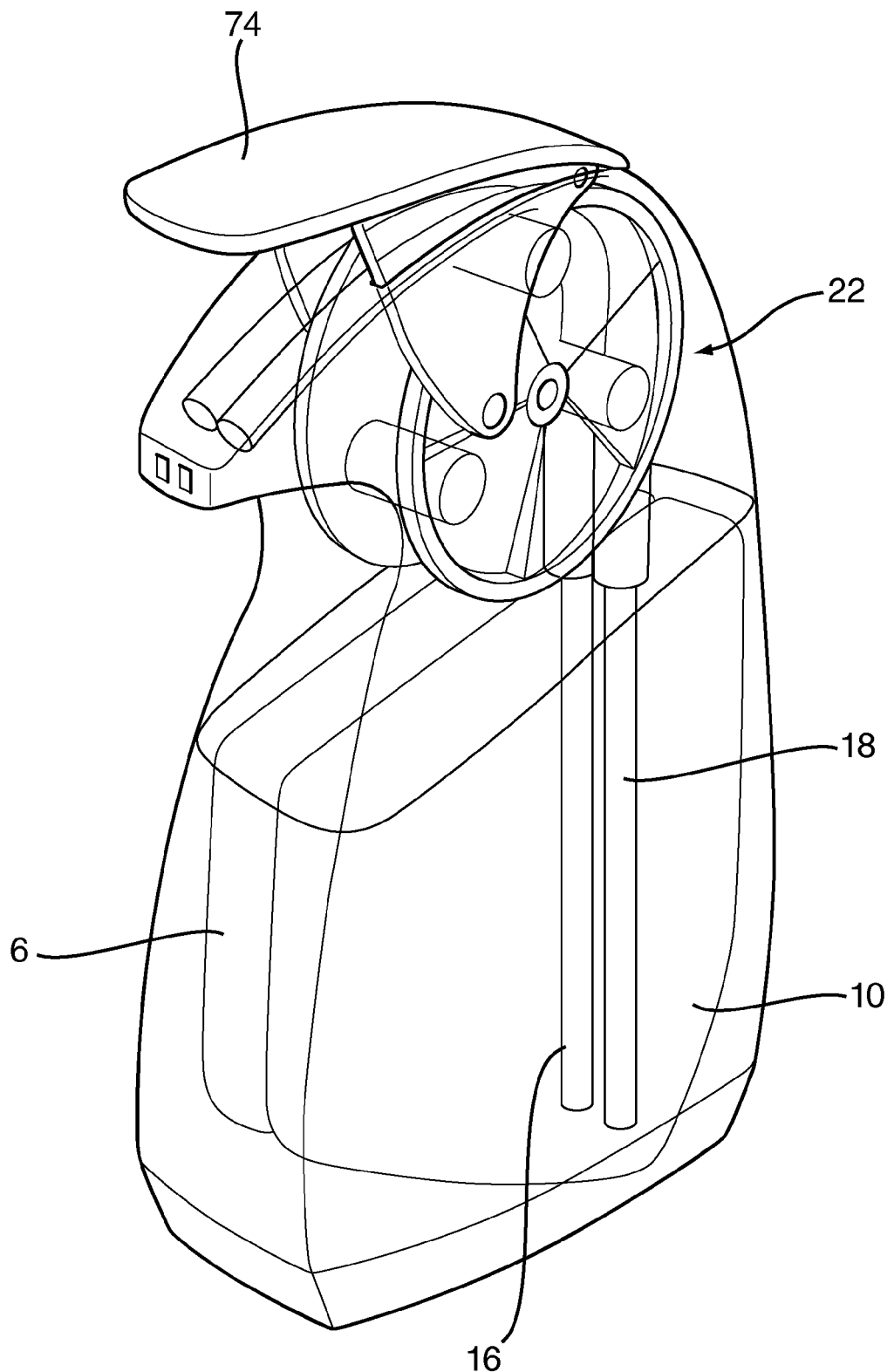

In the embodiment of FIG. 17, an alternative hand-operated trigger lever 74 is used to drive the peristaltic pump head 22.

The invention allows plural volumes of reagents to be evenly pumped as equal volumes from two or more sources irrespective of differences in viscosity, to form a sterilising composition.

Another advantage of the invention over conventional multi-component fluid pumps is that it ensures clean delivery of each reagent fluid. Prior art sterilant apparatuses typically have pistons and require use of silicone oil or a similar lubricant. Such lubricants can contaminate the fluids being pumped. In the present invention, silicone and other lubricants are not required, and the fluids being pumped are isolated from contact with the pump member.

Although the invention has been described with particular reference to a disposable sterilant system, it will be understood that it is not limited to this embodiment. Instead of a finger-operated trigger, the peristaltic pump member may be actuated by a motorised trigger. The trigger may be manually operated by a user, or may be operated automatically in response to a proximity sensor detecting when an object is brought sufficiently close to the nozzle or nozzles. Such embodiments may include a counter-top dispenser, an automatic wall-mounted dispenser, and a personal (body-mounted) dispenser.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable combination.

The invention claimed is:

1. A multi-part sterilant system comprising:
a first part comprising a first reagent in a carrier medium in a first container;
a second part comprising a second reagent in a carrier medium in a second container;
wherein the first reagent and the second reagent will react to provide a sterilising composition when the first part is mixed with the second part;
a pump head having a peristaltic pump member;
the first container having a first-part dispensing tube extending from an interior of the first container and disposed through the pump head;
the second container having a second-part dispensing tube extending from an interior of the second container and disposed through the pump head;
wherein the peristaltic pump member, when actuated, acts on both the first-part dispensing tube and the second-part dispensing tube so as simultaneously to pump substantially equal volumes of the first part and the second part.

2. A system according to claim 1, wherein the peristaltic pump member is driven by a ratchet member provided with a plurality of ratchet surfaces which are engageable by a pawl.

3. A system according to claim 2, wherein the peristaltic pump member is provided with 4-30 ratchet surfaces.

4. A system according to claim 2, wherein the peristaltic pump member is provided with 4-20 ratchet surfaces.

5. A system according to claim 1, wherein the system is incorporated in one of a counter top dispenser, an automatic wall-mounted dispenser, a foot-operated dispenser, a hand-operated dispenser, and a personal, body-mounted, dispenser.

6. A system according to claim 1, which has from two to 10 dispensing tubes.

7. A system according to claim 1, further comprising:
a third part comprising a fluid in a third container;
the third container having a third dispensing tube extending from an interior of the third container and disposed through the pump head;
wherein the peristaltic pump member when actuated acts on the first-part dispensing tube, the second-part dispensing tube and the third dispensing tube so as simultaneously to pump substantially equal volumes of the first part, the second part and the third part.

8. A system according to claim 7, wherein the first reagent and the second reagent will react when mixed to produce an oxidising sterilant composition, and wherein the third part comprises an alcohol or mixture of alcohols.

9. A system according to claim 1, wherein the first container and the second container are collapsible.

10. A system according to claim 1, wherein at least two first-part dispensing tubes and at least two second-part dispensing tubes are provided for dispensing, respectively, the first part and the second part.

11. A system according to claim 1, wherein the first reagent and the second reagent react to produce chlorine dioxide when the first part is mixed with the second part.

12. A system according to claim 1, wherein the first container and the second container are permanently secured to the pump head so that they are not refillable.

13. A system according to claim 1, wherein each container is provided in a housing which is releasably secured to the pump head.

14. A system according to claim 13, wherein each container is collapsible and is secured to a collar member, the collar member having, for each container, an opening which is aligned with an opening of the container to receive a corresponding dispensing tube when the pump head is attached to the housing.

15. A system according to claim 14, wherein the open end of each container has a neck portion and a lip, and wherein each opening in the collar member is dimensioned to support the lip of a container and has a slot portion which extends to an edge of the collar member for slidably receiving the neck portion of a container.

16. A refill component for a multi-part sterilant system, the refill component comprising
a first part comprising a first reagent in a carrier medium in a first collapsible container;
a second part comprising a second reagent in a carrier medium in a second container;
wherein the first reagent and the second reagent will react to provide a sterilising composition when the first part is mixed with the second part;
each container being secured to a collar member, the collar member having, for each container, an opening which is aligned with an opening of the container to receive a corresponding dispensing tube from a pump head.

17. A refill component according to claim 16, wherein the open end of each container has a neck portion and a lip, and wherein each opening in the collar member is dimensioned to support the lip of the container and has a slot portion which extends to an edge of the collar member for slidably receiving the neck portion of the container.

* * * * *